United States Patent
Jadhav et al.

(10) Patent No.: US 7,531,187 B2
(45) Date of Patent: May 12, 2009

(54) SYNERGISTIC INSECTICIDAL COMPOSITION CONTAINING CHLORONICOTYNYLE AND PYRETHROIDS COMPOUNDS

(75) Inventors: Prakash Mahadev Jadhav, Maharashtra (IN); Jaidev Rajnikant Shroff, Maharashtra (IN)

(73) Assignee: United Phosphorus, Ltd., Mumbai (IN)

( * ) Notice: Subject to any disclaimer, the term of this patent is extended or adjusted under 35 U.S.C. 154(b) by 0 days.

(21) Appl. No.: 10/889,213

(22) Filed: Jul. 13, 2004

(65) Prior Publication Data

US 2006/0014724 A1    Jan. 19, 2006

(51) Int. Cl.
*A01N 25/32* (2006.01)

(52) U.S. Cl. .................. 424/406; 424/405; 424/407; 424/409; 424/417; 424/418; 424/419; 424/420; 424/421; 514/341; 514/521

(58) Field of Classification Search ................. 514/531, 514/519; 424/405, 408, 409, 421
See application file for complete search history.

(56) References Cited

U.S. PATENT DOCUMENTS 5,719,103 A * 2/1998 Dao et al. .................. 504/361
6,660,690 B2 * 12/2003 Asrar et al. ................. 504/100

FOREIGN PATENT DOCUMENTS

FR 2784011 4/2000
WO WO0230200 * 4/2002

* cited by examiner

*Primary Examiner*—Neil Levy
(74) *Attorney, Agent, or Firm*—Jones, Tullar & Cooper, P.C.

(57) ABSTRACT

A synergistic insecticidal composition is formed containing a Chloronicotynyle compound and a Pyrethroids compound. The Chloronicotynyle compound is provided in an amount preferably ranging from 0.1 to 5.0% by weight of the synergistic insecticidal composition. The Pyrethroids compound is provided in an amount preferably ranging from 1 to 60% by weight of the synergistic insecticidal composition. The synergistic insecticidal composition also preferably includes 35 to 98.90% by weight of conventional agriculturally acceptable carrier(s) and/or excipients.

42 Claims, No Drawings

SYNERGISTIC INSECTICIDAL COMPOSITION CONTAINING CHLORONICOTYNYLE AND PYRETHROIDS COMPOUNDS

BACKGROUND OF THE INVENTION

1. Field of the Invention

The present invention relates to a synergistic insecticidal composition containing a Chloronicotynyle compound and a Pyrethroids compound and a process for preparing the synergistic insecticidal composition.

2. Description of Related Art

Enhancement of agricultural produce requires the protection of the crops and its produce from pest damage. Various chemicals and their formulations have been developed and are in use currently for the effective management of insects and pests. Due to non-judicious use of the hitherto known pesticides, the pests gain resistance and become hard to kill. Physically compatible pesticide mixtures exhibit a better pest management. These mixtures show multifaceted advantages than when applied individually, providing a synergistic effect.

The need for more food has to be met through higher yields per unit of land, water, energy and time. Excessive use of mineral fertilizers and chemical pesticides has caused soil degradation, ground water pollution and the spread of the pest's resistant to pesticides in several areas. Hence their judicious use includes avoiding prophylactic sprays, adopting strip treatment, spot application to only those areas with heavy incidence of pests, application to the soil to avoid direct contact with the natural enemies and using selective or non-persistent pesticides. The systemic pesticides are sprayed at a concentration of 0.02 to 0.05 percent active ingredient. The contact pesticides are sprayed at 0.05 to 0.07 or even 0.1 percent active ingredient. The soil application of the granular systemic insecticides varies from 1 to 2 kg a.i./ha. The fungicides are applied up to 2 g/l depending upon the chemical used, pest species and season of the application.

Processes for insecticidal agents and compositions have been developed to control insect pests and in practice have been used as a single or a mixed agent. However, processes for the economically efficient and ecologically safe insect control compositions are still being sought. A process for the preparation of insecticidal compositions which allows for reduced effective dosage rates, increased environmental safety and lower incidence of insect resistance are highly desirable. Although the rotational application of insect control agents having different modes of action may be adopted for good pest management practice, this approach does not necessarily give satisfactory insect control. Further, even though combinations of insect control agents have been studied, a high synergistic action has not always been found. Obtaining an insecticidal composition which demonstrates no cross-resistance to existing insecticidal agents, no toxicity problems and little negative impact on the environment is extremely difficult.

Thus there is a need to develop and improve insecticidal compositions to increase agricultural yield. The composition should have high synergistic action, no cross resistance to existing insecticidal agents, avoid excess loading of the toxicant to the environment and negligible impact to environmental safety. A need also exists for synergistic insecticidal compositions which could be physico- compatible formulations in the form of storage stable, safely packed, ready to use formulation.

BRIEF SUMMARY OF THE INVENTION

The present invention achieves the above objectives by providing a synergistic insecticidal composition containing a Chloronicotynyle compound and a Pyrethroids compound. The present invention is also directed to a process for making a synergistic insecticidal composition containing a Chloronicotynyle compound and a Pyrethroids compound.

The synergistic insecticidal composition containing the Chloronicotynyle compound and the Pyrethroids compound has a variety of advantages including those provided herein. The synergistic insecticidal composition is especially useful for the control of agricultural pests and hygienic pests. The synergistic insecticidal composition is highly effective for the protection of growing plants including: cotton, paddy, rice forage crops, sugarcane, cole crops, leafy vegetables, tobacco, tomatoes, potatoes, flowering ornamentals, vine crops and fruit trees from the ravages of insects. The synergistic insecticidal composition is found to be highly active against a wide variety of chewing, boring and sucking insects, e.g. Aphids, thrips, lepidopterous larvae, sawflies, leafminers, leafhoppers, cutworms, whiteflies, soil insects, termites and some species of biting insects, such as rice water weevil on Colarado beetle etc. The synergistic insecticidal composition of the present invention also demonstrates a high controlling effect with reduced crop protection cost, increased crop yield and reduced environmental load. The synergistic insecticidal composition is useful for synergistic insect control and enhanced crop protection. The synergistic insecticidal composition also delays the dominance of the resistant strains of pests, has a broader spectrum of activity and reduces risk of developing resistance. The synergistic insecticidal composition can achieve effective and economic control of undesirable species. Yet another advantage of the synergistic insecticidal composition is that it can improve biological performance in a single application and minimize occupational exposure and hazards. Still another advantage of the present synergistic insecticidal composition is that it decreases the cost of application, saves fuel cost, labour cost and applicator's precious time and is therefore very economical. The synergistic insecticidal composition also reduces the wear of equipment and losses caused by mechanical damage to crops and soil.

Another objective of the present invention is to provide a process for preparing the synergistic insecticidal composition containing a Chloronicotynyle compound and a Pyrethroids compound. The advantage of the process for preparing the synergistic insecticidal composition relates to the propagation product of the plants, and especially the seed, coated with and/or containing the Chloronicotynyle compound and the Pyrethroids compound as defined above or a composition containing the mixture of those two active ingredients or a mixture of two compositions each providing one of the above-mentioned two active ingredients. It will easily be understood that the seed can be treated either with a composition comprising a Pyrethroids compound, preferably Cypermethrin, Fenvalerate, Permethrin, then with a composition comprising a Chloronicotynyl compound, preferably Imidacloprid, Acetamiprid, or vice versa, or with a composition containing the two active ingredients.

DETAILED DESCRIPTION OF THE INVENTION

The present invention provides a synergistic insecticidal composition containing a Chloronicotynyle compound and a Pyrethroids compound (also referred to herein as "active ingredients"). A synergistically effective amount of one or more compounds falling within a group of Chloronicotynyle compounds is an amount preferably ranging from 0.1 to 5.0% by weight of the synergistic insecticidal composition, more preferably in the range of 0.5 to 5.0% of Chloronicotynyle compounds by weight of the synergistic insecticidal composition. The Chloronicotynyle compound is preferably selected from a group consisting of Imidacloprid, Nitenpyram, and Acetamiprid, preferably Imidacloprid, which may be Technical grade and has a purity of 95% minimum. The Chloronicotynyle compound is provided in combination with one or more compounds selected from a group of Pyrethroids compounds provided in an amount preferably ranging from 1 to 60% by weight of the synergistic insecticidal composition, more preferably in the range of 2.5 to 50% of Pyrethroids compounds by weight of the synergistic insecticidal composition. The Pyrethroids compounds are preferably selected from a group consisting of acrinathrin, allethrin, bifenthrin, bioallethrin, cyfluthrin, cyhalothrin, lambda cyhalothrin, Cypermethrin, alpha cypermethrin, beta cypermethrin, zeta cypermethrin, deltamethrin, permethrin, and more preferably Cypermethrin having a purity of 92% minimum, Fenvalerate having a purity of 92% minimum, and Permethrin having a purity of 92% minimum. The amounts of the Choloronicotynyle compound and the Pyrethroids compound used in the synergistic insecticidal composition may vary accordingly to prevailing conditions such as the particular compounds present, insect pest attack strength, type of pests, application timing, weather conditions, soil conditions, mode of application, topographical character, target crop and the like.

The synergistic insecticidal composition also preferably includes 35 to 98.90% by weight of conventional agriculturally acceptable carrier(s) and/or excipients. An agriculturally acceptable carrier(s) may be a natural or synthetic, inorganic or organic substance with which the active ingredient is combined to facilitate its application to the plant, to seeds or to the soil. The carrier(s) is therefore generally inert and must be agriculturally acceptable, especially on the plant treated. The carrier(s) may be in the form of a solid, a liquid or both. Solid carries are essentially: mineral earth such as silicas, silica gels, silicates, talc, kaolin, montmorillonite, attapulgite, pumice, sepiolite, bentonite, limestone, lime, chalk, bole, loes, clay, dolomite, diatomaceous earth, calcite, calcium sulfate, magnesium sulfate, magnesium oxide, sand, ammonium sulfate, ammonium phosphate, ammonium nitrate, and crushed products of vegetable origin such as cereal meal, tree bark meal, wood meal and nutshell meal, cellulose powders, or other solid carriers. Liquid carrier(s) are liquid solvents, aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; aromatic hydrocarbon solvents. Gaseous carrier(s) are liquified gaseous extenders or carriers that are gaseous at ambient temperature and under atmospheric pressure, for example aerosol propellant, such as halogenated hydrocarbons as well as butane, propane, nitrogen and carbon dioxide, water, alcohols, ketones, petroleum fractions, aromatic or paraffinic hydrocarbons, chlorinated hydrocarbons, liquefied gases, etc.

The synergistic insecticidal composition optionally includes surfactant(s) which are preferably non-ionic, cationic and/or anionic in nature and surfactant mixtures which have good emulsifying, dispersing and wetting properties, depending on the nature of the active ingredient to be formulated. Suitable anionic surfactants can be both so-called water-soluble soaps and water-soluble synthetic surface-active compounds. Soaps which may be used are the alkali metal, alkaline earth metal or substituted or unsubstituted ammonium salts of higher fatty acids ($C_{10}$-$C_{22}$), for example the sodium or potassium salt of oleic or stearic acid, or of natural fatty acid mixtures. The surfactant can be an emulsifier, dispersant or wetting agent of ionic or nonionic type. Examples which may be used are salts of polyacrylic acids, salts of lignosulphonic acids, salts of phenylsulphonic or naphthalenesulphonic acids, polycondensates of ethylene oxide with fatty alcohols or with fatty acids or with fatty amines, substituted phenols, especially alkylphenols, sulphosuccinic ester salts, taurine derivatives, especially alkyltaurates, or phosphoric esters of polyethoxylated phenols or alcohols. The presence of at least one surfactant is generally essential when the active ingredient and/or the inert carrier are insoluble in water and the vehicle for the application is water.

The synergistic insecticidal composition containing the Chloronicotynyle compound and the Pyrethroids compound can be converted into customary formulations, such as solutions, emulsions, suspensions, powders, foams, pastes, granules, aerosols, active-compound-impregnated natural and synthetic materials, very fine encapsulations in polymeric substances and in coating compositions for seed. Furthermore, the synergistic insecticidal composition may be in formulations with smokes, such as fumigating cartridges, fumigating cans, fumigating coils and the like, and also ULV cold mist and warm mist formulations. These formulations are prepared in a known manner, for example by mixing the active ingredients with extenders, that is, liquid solvents, pressurized liquefied gases and/or solid carriers, optionally with the use of surface-active agents, that is, emulsifying agents and/or dispersing agents and/or foam-forming agents. In the case of the use of water as an extender, organic solvents can, for example, also be used as auxiliary solvents. As liquid solvents, the following ingredients may be used including suitable aromatics, such as xylene, toluene or alkylnaphthalenes; chlorinated aromatics or chlorinated aliphatic hydrocarbon, such as chlorobenzenes, chloroethylenes or methylene chloride; aliphatic hydrocarbons, such as cyclohexane or paraffins, for example mineral oil fractions; aromatic hydrocarbon solvents such as C-IX, Solvesso (100, 150, 200), Aromax; alcohols such as butanol or glycol as well as their ethers and esters, ketones such as acetone, methyl ethyl ketone, methyl isobutyl ketone of cyclohexanone; strongly polar solvents, such as dimethylformamide and dimethyl sulphoxide, as well as water. Liquefied gaseous extenders or carriers that may be used are preferably those that are gaseous at ambient temperature and under atmospheric pressure, for example aerosol propellant, such as halogenated hydrocarbons as well as butane, propane, nitrogen and carbon dioxide. Solid carriers there are suitable preferably include ground natural minerals, such as kaolins, clays, talc, chalk, quartz, attapulgite, montmorillonite or diatomaceous earth, and ground synthetic minerals, such as finely divided silica, alumina and silicates. Solid carriers for granules that are suitable preferably include crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks. Emulsifying and/or foam-forming agents there are suitable preferably include nonionic and anionic emulsifiers, such as polyoxytheylene fatty acid esters, Polyoxyethylene fatty alcohol ethers, for example alkylaryl polyglycol ethers, alkylsulphonates, alkyl sulphates, arylsulphonates as well as protein hydrolysates. Dispersing agents that are suitable preferably include ligninsulphite waste liquors and methylcellulose.

The synergistic insecticidal composition may optionally include adhesives, preferably carboxymethylcellulose and natural and synthetic polymers in the form of powders, polyvinylpyrrolidone, granules or lattices, such as gum Arabic, polyvinyl alcohol and polyvinyl acetate, as well as natural phospholipids such as cephalins and lecithins, and synthetic phospholipids, can be used in the formulations. Further additives may be mineral and vegetable oils.

The synergistic insecticidal composition may optionally include colorants such as inorganic pigments for example iron oxide, titanium oxide and Prussian Blue, and organic dyestuffs, such as alizarin dyestuffs, azo dyestuffs and metal phthalocynanine dyestuffs and trace nutrients such as salts of iron, magnese, boron, copper, cobalt, molybdenum and zinc.

Formulations containing the synergistic insecticidal composition preferably have between 0.1 and 65 percent by weight of the synergistic insecticidal composition, more preferably between 1.1 and 65%.

According to the present invention there is provided a process for preparing a synergistic insecticidal composition by mixing thoroughly the following ingredients: 1) one or more Chloronicotynyle compounds in an amount preferably ranging from 0.1 to 5% by weight of the composition, more preferably in the range of 0.5 to 5.0% of Chloronicotynyle compounds; 2) one or more Pyrethroids compounds in an amount preferably ranging from 1 to 60% by weight of the composition, more preferably in the range of 2.5 to 50% of Pyrethroids compounds and 3) conventional agriculturally acceptable excipient(s) and or carrier(s) in an amount preferably ranging from 35 to 98.9% by weight of the synergistic insecticidal composition. The Chloronicotynyle compounds and the Pyrethroids compounds are those stated previously for use in the synergistic insecticidal composition. The Chloronicotynyle compound is preferably selected from the group consisting of Imidacloprid, Acetamiprid, and Nitenpyram, and more preferably Imidacloprid and acetamiprid which may be technical grade and have a purity of 95% minimum. The Pyrethroids compound is preferably selected from the group consisting Cypermethrin, Fenvalerate, Permethrin, Allethrin, Bifenthrin, Cyhalothrin, Deltamethrin, more preferably Cypermethrin having a purity of 92% minimum, Fenvalerate having a purity of 92% minimum and Permethrin having a purity of 92% minimum.

The process of the present invention optionally includes intensive mixing and/or milling of the active ingredients with other substances, such as a stabilizer, an emetic agent, a disintegrating agent, an antifoaming agent, a wetting agent, a dispersing agent, a binding agent, dye(s), fillers, carriers, surface active compounds (surfactants), and optionally solid and/or liquid auxiliaries and/or adjuvants such as wetters, adhesives, dispersants or emulsifiers.

The name "Acetamiprid" describes a chemical substance having a molecular weight 222.7; is in the form of colourless crystals, m.pt. 98.9° C.; solubility in water at 25° C., 4200 mg/l. Soluble in acetone, methanol, ethanol, dichloromethane, chloroform, acetonitrile and tetrahydrofuron. Stable in buffered solutions at pH 4,5,7. Degraded slowly at pH 9 and 45° C. Stable under sunlight. The molecule has following formula:

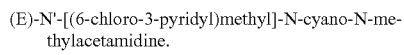

(E)-N'-[(6-chloro-3-pyridyl)methyl]-N-cyano-N-methylacetamidine.

It is a systemic insecticide for soil and foliar application. It controls Hemiptera, especially aphids, Thysanoptera and Lepidoptera on wide range of crops, especially vegetables, fruits and tea. Its acute oral LD50 for male rats 217, female rats 146, male mice 198, female mice 184 mg/Kg. Acute percutaneous LD50 for male and female rats>2000 mg/Kg. Non irritating to skin and eyes (rabbits) During inhalation LC50 (4 h) for male and female rats is about>0.29 mg/l.

The name "Imidacloprid" describes a chemical substance having a molecular weight 255.7; is in the form of colourless crystals with a weak characteristic odour, m.pt. 144° C.; solubility in water at 20° C., 0.61 g/l. In dichloromethane 55, isopropanol 1.2, toluene 0.68, n.hexane<0.1 (all in g/l. 20° C.). Stable to hydrolysis at pH 5-11. The molecule has following formula:

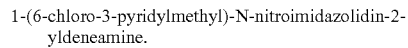

1-(6-chloro-3-pyridylmethyl)-N-nitroimidazolidin-2-yldeneamine.

It acts on the central nervous system, causing blockage of postsynaptic nicotinergic acetylcholine receptors. It is a systemic insecticide with contact and stomach action. Readily taken up by the plant and further distributed acropetally, with good root-systemic action. It controls the sucking insects, including rice-hoppers, aphids, thrips and whiteflies. Also effective against soil insects, termites and some species of biting insects, such as rice water weevil and Colorado beetle. It has no effect on nematodes and spider mites. Used as seed dressing, as soil treatment and as foliar treatment in different crops, e.g. rice, cotton, cereals maize sugar beet, potatoes, vegetables citrus fruit, pome fruit and stone fruit. Its acute oral LD50 for male and female rats 450, mice 150 mg/Kg. Acute percutaneous LD50 (24 h) for rats>5000 mg/Kg. Non irritating to skin and eyes (rabbits). Not a skin sensitiser. During inhalation LC50 (4 h) for female rats is>5323 mg/m³ air (aerosol). Not mutagenic or teratogenic.

Descriptions of the above-listed commercially available compounds may be found in "The Pesticide Manual" 11th Edition, British Crop Protection Council (1997) among other publications.

The Pyrethroids compounds have high insecticidal and acaricidal activity; have wide spectrum of the action on plant pests; low persistence and breakdown to form products non-toxic to human and animals; systemic action of a number of the compounds; low dosage of the compound per unit area treated; relatively rapid metabolism in vertebrate organism and absence of accumulation in their bodies, and also comparatively low chronic toxicity; and rapidity of action on plant pests. The preferred compounds for use as a Pyrethroids compounds are Cypermethrin and Permethrin.

The name 'Cypermethrin', an insecticide belonging to a synthetic pyrethroid group, describes a chemical substance having a solubility in water of 0.004 mg/l (at pH7); corresponds to a mixture of cis and trans isomers having following formula:

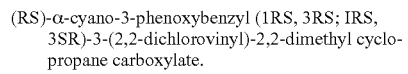

(RS)-α-cyano-3-phenoxybenzyl (1RS, 3RS; IRS, 3SR)-3-(2,2-dichlorovinyl)-2,2-dimethyl cyclopropane carboxylate.

So being almost insoluble in water, it is soluble in acetone, chloroform, cyclohexanone, xylene >450 (g/l); ethanol 337 (g/l), hexane 103 (g/l) at 20° C. Cypermethrin is presently recognized as a non-systemic insecticide with contact and stomach action. It also exhibits antifeeding action and good residual activity on treated plants. It is used to control a wide range of insects, especially Lepidoptera, but also Coleoptera, Dipetera, Hemiptera and other classes in fruits (including Citrus), Vines, Vegetables, Potatoes, Cucurbits, Lettuce, Capsicums, tomatoes, cereals, maize, soyabeans, cotton, coffee, Cocoa, rice, peacans, oilseed rape, beet, ornamentals, forestry, etc. It is also used for control of flies and other insects in animal houses; and mosquitoes, Cockroaches, houseflies and other insect, pests in public health. It is also used as an animal ectoparasiticide.

The name "Fenvalerate" describes a chemical substance having a molecular weight 419.9; is in the form of a viscous yellow-brown liquid, sometimes partly crystallized at room temperature; Solubility at 20° C.: <1 mg/l water; at 23° C.: >1 kg/kg acetone, chloroform, cyclohexanone, ethanol, xylene; 155 g/kg hexane. It is stable to heat and sunlight. It is more stable in acid than in alkaline media, with optimum stability at pH 4. The molecule has the following formula:

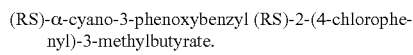
(RS)-α-cyano-3-phenoxybenzyl (RS)-2-(4-chlorophenyl)-3-methylbutyrate.

Fenvalerate is a highly active contact insecticide effective against a wide range of pests, including strains resistant to Organochlorine, Organophosphorus and carbamate insecticides. It controls insects that attack leaves or fruits on various crops, including cotton, fruit, vegetables and vines, at 25-250 g a.i./ha, and is persistent under various field conditions. It is also used in public health and animal husbandry, controlling flies in cattle sheds for 60 days at 110 mg/aquare meter wall, an is effective against cattle ticks at 200-300 mg/l. acute oral $LD_{50}$ for rats 451 mg/kg; for domestic fowl>1600 mg/kg. Acute percutaneous $LD_{50}$ for rats>5000 mg/kg.

The name "Permethrin" describes a chemical substance having a molecular weight 391.3; is in the form of a viscous yellow-brown liquid, which sometimes tends to crystalline partly at room temperature ; Solubility at 30° C.: 0.2 mg/l water; at 25° C.:>1 kg/kg hexane; 258 g/kg methanol; >/=1 kg/kg Xylene. It is stable to heat (>/=2 years at 50° C.), is more stable in acid than alkaline media with optimum stability at pH 4. Some photochemical degradation has been observed in laboratory studies but field data indicates this does not adversely affect biological performance. Pure Permethrin has m.p. 34-39° C., the cis-isomer m.p. 63-65° C., the trans-isomers m.p. 44-47° C. The molecule has following formula:

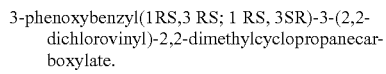
3-phenoxybenzyl(1RS,3 RS; 1 RS, 3SR)-3-(2,2-dichlorovinyl)-2,2-dimethylcyclopropanecarboxylate.

It is a contact insecticide effective against a broad range of pests. It controls leaf- and fruit-eating lepidopterous and coleopterous pests in cotton at 100-150 g a.i./ha, in fruits at 25-50 g/ha, in tobacco, vines and other crops at 50-200 g/ha, in vegetables at 40-70 g/ha. It has good residual activity on treated plants. It is effective against a wide range of animal ectoparasites, provide <60 days residual control of biting flies in animal housing at 200 mg a.i. (as EC)/square meter wall or 30 mg a.i. (as WP)/m² wall and is effective as a wool preservative at 200 mg/kg wool. It provides>120 days control of cockroaches and other crawling insets at 100 mg a.i. (as WP)/m². Oral $LD_{50}$ values of Permethrin depend on such factors as: carrier, cis/trans ratio of the sample, the test species, its sex, age and degree of fasting. Values reported sometimes differ markedly. Typical oral $LD_{50}$ values for cis/trans ratio of 40:60 are for rats 430-4000 mg/kg; for mice 540-2690 mg/kg; for chicken>300 mg/kg; for Japanese quail>13500 mg/kg.

Pesticidal compositions are often formulated and transported in a concentrated form which is subsequently diluted by the user before application. The presence of small amounts of a surfactant facilitates this process of dilution. Thus, preferably the synergistic insecticidal composition according to the present invention comprises, if desired, at least one surfactant. For example, the synergistic insecticidal composition may contain one or more carriers and at least one surfactant.

The synergistic insecticidal composition may optionally include a carrier which is any material with which the active ingredient is formulated to facilitate application to the locus to be treated, which may for example be a plant, seed or soil, or to facilitate storage, transport or handling. The preferred carrier may be a solid or a liquid, including a material which is normally a gas but which has been compressed to form a liquid or a combination thereof. The synergistic insecticidal composition may also contain other additive such as stabilizers, surfactants, emulsifiers, defoamers, buffers, thickeners, dyes, extenders, emetic agent(s) and the like.

Surprisingly, it has been found that the synergistic insecticidal composition prepared by the process of the present invention has superior insect control at lower levels of the combined concentrations of the active agents employed than that may be achieved when the active ingredients are applied alone. In other words, the process of preparing the synergistic insecticidal composition of the present invention and the synergistic insecticidal composition resulting therefrom is not a mere admixture of the active ingredients resulting in the aggregation of the properties of the active ingredients employed in the synergistic insecticidal composition. The process involves judicial selection of the appropriate amounts of the active ingredients which combination alone imparts synergism to the resulting synergistic insecticidal composition providing the unexpected and unique properties Advantageously, known adjuvants like PBO, Piperonyl botooxide, which are used to enhance the activity of the Pyrethroids compounds, may preferably be incorporated in the process of preparing the synergistic insecticidal composition. The synergistic insecticidal composition resulting from the process may be dispersed in a solid or liquid diluent for application to the insect, its food supply, breeding ground or habitat as a dilute spray or as a solid dust or dust concentrate.

As a commodity the synergistic insecticidal composition is generally in a ready to use form which may be diluted at the place of application for suitable concentration of the active ingredients.

In general, the synergistic effect may be achieved at application rates of the active ingredient of about 20 to 25 g/ha of Imidacloprid in combination with 10 to 75 g/ha of Cypermethrin; preferably in about 1 to 250 g/ha. In general, the synergistic effect may be achieved at application rates of the active ingredient of about 20 to 25 g/ha of Imidacloprid in combination with 10 to 150 g/ha of Fenvalerate; preferably in about 0.5 to 750 g/ha.

Preferred combination of the synergistic insecticidal composition prepared by the process of the present invention are those combination wherein the active ingredient ratio (weight/weight) of the Chloronicotynyle compound:Pyrethroids compound is about 1:1 to 1:1000. More preferred combination of the invention are combination of the Chloronicotynyle compound, including Imidacloprid, Acetamiprid, and Nitenpyram, and the Pyrethroids compound, including Cypermethrin and Permethrin, wherein the active ingredient ratio (weight/weight) of the Chloronicotynyle compound:Pyrethroids compound is about 1:1 to 1:600, most preferred is about 1:2 to 1:600.

Advantageously, the Chloronicotynyle compound or a mixture thereof may be formulated with a second insecticidally effective ingredient alone or a mixture thereof and optionally other agriculturally acceptable carriers and formulation adjuvants. Said formulation may be dispersed in a solid or liquid diluent for application to the insect, its food supply, breeding ground or habitat as a dilute spray or as a solid dust or dust concentrate.

As a commodity the synergistic insecticidal composition may preferably be in a concentrated form, more preferably 1.01 to 65%, whereas the end user generally employs diluted compositions. The synergistic insecticidal composition may be diluted to a concentration down to 0.001% of active ingredient. Preferably, the formulation comprises approximately from 1.01 to 65% by weight of active ingredients. The doses usually are in the range from 0.01 to 10 kg a.i./ha. A preferred ratio of the essential active ingredients of the synergistic insecticidal composition is about 0.1-5.0 weight part of Chloronicotynyle compounds to about 1-60 weight parts of one or more compounds selected from the Pyrethroids compounds.

A preferred emulsifiable concentrate, wettable powder, dry flowable granular composition may contain by weight about 1.01% to 65% active ingredients preferably Imidacloprid and/or Acetamiprid in combination with Cypermethrin, Fenvalerate and/or Permethrin.

The forms of application of the synergistic insecticidal depend on the intended purposes; in any case, they guarantee a uniform distribution of the active ingredients. They can be applied, for example, in the form of directly sprayable aqueous solutions, powders, suspensions, also highly-concentrated aqueous suspensions or dispersions, dusts, materials for spreading or granules, by spraying, atomizing, dusting or pouring. Aqueous use forms can be prepared from powders, emulsifiable conentrates, dry flowable granules by adding water.

Alternatively, concentrates which consist of insecticidally active ingredients, wetter, adhesive, dispersant or surfactants and, if appropriate, solvent or oil may be prepared, and such concentrates are suitable for dilution with water.

Aqueous dispersions and suspensions, for example, synergistic insecticidal compositions obtained by diluting the formulated product with water, also lie within the scope of the invention.

The biological activity of the active ingredient can also be increased by including an adjuvant in the formulations. An adjuvant is defined herein as a substance which can increase the biological activity of an active ingredient but is not itself significantly biologically active. The adjuvant can either be included in the formulation as a co-formulant or carrier, or can be added to the spray tank together with the formulation containing the active ingredient.

In actual practice, the synergistic insecticidal composition may be applied to the plant foliage or plant stem or to the insect habitat or to the locus of a hygienic pest as a dilute spray prepared from any of the above-said formulations.

The synergistic effective amount of the combination of the Chloronicotynyle compound, preferably Imidacloprid and Acetamiprid, and the Pyrethroids compound, preferably Cypermethrin and Permethrin, may vary accordingly to prevailing conditions such as the particular compound present, insect pest attack strength, type of pests, application timing, weather conditions, soil conditions, mode of application, topographical character, target crop and the like.

Following the right use of the synergistic insecticidal composition with a formulation having a multi-pesticide components, such as pesticide mixture, formulations prepared with extra care of physical compatibility by purposefully specially selecting solvents, carriers and the surfactants, thickeners, stabilizers, etc. exhibits better pest management.

These and other advantages of the invention may become more apparent from the examples set forth herein below.

These examples are provided merely as illustrations of the invention and are not intended to be construed as a limitation thereof.

EXAMPLE-1

Preparation of a synergistic insecticidal composition containing Imidacloprid 4.5%+Cypermethrin 15.0[19.5% WP]:

Composition

| Ingredient | Quantity (% w/w) |
| --- | --- |
| Imidacloprid Techical (purity 95%) | 4.7400 |
| Cypermethrin Technical (purity 92%) | 16.3000 |
| Stabilizer (PBO) | 0.1000 |
| Emetic agent (Bitrex) | 0.0002 |
| Dipersing agent (Morwet D425) | 5.0000 |
| Wetting agent (Supragil WP) | 3.0000 |
| Dye(s) | 0.0500 |
| Fillers (s) (Wessalon-S and Kaolex) | 70.8098 |
| Total | 100.00% (w/w) |

Process for the preparation of the above said synergistic insecticidal composition comprises mixing thoroughly, for ½ hour, Imidacloprid, PBO, Bitrex, Morwet D425, Supragil WP, Wessalon-S, Kaolex, Cypermethrin and Rhodamine-B in a pre-blender equipped with an agitator to get a homogenous mixture of all the ingredients. Thereafter, the homogenous mixture obtained is micronised to get a particle size of 2-10 microns which is post-blended to yield the synergistic insecticidal composition

EXAMPLE-2

Preparation of a synergistic insecticidal composition containing Acetamiprid 2.0%+Cypermethrin 10.0[12.0% WP]:

Composition

| Ingredient | Quantity (% w/w) |
| --- | --- |
| Acetamiprid Techical (purity 95%) | 2.1100 |
| Cypermethrin Technical (purity 92%) | 10.8696 |
| Stabilizer (PBO) | 0.1000 |
| Emetic agent (Bitrex) | 0.0002 |
| Dipersing agent (Morwet D425) | 5.0000 |
| Wetting agent (Supragil WP) | 3.0000 |
| Dye(s) | 0.0500 |
| Fillers (s) (Wessalon-S and Kaolex) | 78.8702 |
| Total | 100.00% (w/w) |

Process for the preparation of the above said synergistic insecticidal composition comprises mixing thoroughly, for ½ hour, Acetamiprid, PBO, Bitrex, Morwet D425, Supragil WP, Wessalon-S, Kaolex, Cypermethrin and Rhodamine-B in a pre-blender equipped with an agitator to get a homogenous mixture of all the ingredients. Thereafter, the homogenous mixture obtained is micronised to get a particle size of 2-10 microns which is post-blended to yield the synergistic insecticidal composition

EXAMPLE-3

Preparation of a synergistic insecticidal composition containing Imidacloprid 4.0%+Permethrin 20.0% [24.0% WP]:

Composition

| Ingredient | Quantity (% w/w) |
|---|---|
| Imidacloprid Techical (purity 95%) | 4.2100 |
| Permethrin Technical (purity 92%) | 21.7400 |
| Stabilizer (PBO) | 0.2000 |
| Emetic agent (Bitrex) | 0.0002 |
| Dipersing agent (Morwet D425) | 5.0000 |
| Wetting agent (Supragil WP) | 3.0000 |
| Dye(s) | 0.0500 |
| Fillers (s) (Wessalon-S and Kaolex) | 65.7998 |
| Total | 100.00% (w/w) |

Process for the preparation of the above said synergistic insecticidal composition comprises mixing thoroughly, for ½ hour, Imidacloprid, PBO, Bitrex, Morwet D425, Supragil WP, Wessalon-S, Kaolex, Permethrin and Rhodamine-B in a pre-blender equipped with an agitator to get a homogenous mixture of all the ingredients. Thereafter, the homogenous mixture obtained is micronised to get a particle size of 2-10 microns which is post-blended to yield the synergistic insecticidal composition

EXAMPLE-4

Preparation of a synergistic insecticidal composition containing Acetamiprid 2.5%+Permethrin 10[12.5% WP]:

Composition

| Ingredient | Quantity (% w/w) |
|---|---|
| Acetamiprid Techical (purity 95%) | 2.6300 |
| Permethrin Technical (purity 92%) | 10.8696 |
| Stabilizer (PBO) | 0.1000 |
| Emetic agent (Bitrex) | 0.0002 |
| Dipersing agent (Morwet D425) | 5.0000 |
| Wetting agent (Supragil WP) | 3.0000 |
| Dye(s) | 0.0500 |
| Fillers (s) (Wessalon-S and Kaolex) | 78.3502 |
| Total | 100.00% (w/w) |

Process for the preparation of the above said synergistic insecticidal composition comprises mixing thoroughly, for ½ hour, Acetamaprid, PBO, Bitrex, Morwet D425, Supragil WP, Wessalon-S, Kaolex, Permethrin and Rhodamine-B in a pre-blender equipped with an agitator to get a homogenous mixture of all the ingredients. Thereafter, the homogenous mixture obtained is micronised to get a particle size of 2-10 microns which is post-blended to yield the synergistic insecticidal composition.

EXAMPLE-5

Preparation of a synergistic insecticidal composition containing Imidacloprid 2.0%+Fenvalerate 15.0[17.0% WP]:

Composition

| Ingredient | Quantity (% w/w) |
|---|---|
| Imidacloprid Techical (purity 95%) | 2.1100 |
| Fenvalerate Technical (purity 92%) | 16.3000 |
| Stabilizer (PBO) | 0.2000 |
| Emetic agent (Bitrex) | 0.0002 |
| Dipersing agent (Morwet D425) | 5.0000 |
| Wetting agent (Supragil WP) | 3.0000 |
| Dye(s) | 0.0500 |
| Fillers (s) (Wessalon-S and Kaolex) | 73.3398 |
| Total | 100.00% (w/w) |

Process for the preparation of the above said synergistic insecticidal composition comprises mixing thoroughly, for ½ hour, Imidacloprid, PBO, Bitrex, Morwet D425, Supragil WP, Wessalon-S, Kaolex, Fenvalerate and Rhodamine-B in a pre-blender equipped with an agitator to get a homogenous mixture of all the ingredients. Thereafter, the homogenous mixture obtained is micronised to get a particle size of 2-10 microns which is post-blended to yield the synergistic insecticidal composition.

EXAMPLE-6

Preparation of a synergistic insecticidal composition containing Acetamiprid 2.0%+Fenvalerate 18.0[20.0% WP]:

Composition

| Ingredient | Quantity (% w/w) |
|---|---|
| Acetamiprid Techical (purity 95%) | 2.1100 |
| Fenvalerate Technical (purity 92%) | 19.5700 |
| Stabilizer (PBO) | 0.1000 |
| Emetic agent (Bitrex) | 0.0002 |
| Dipersing agent (Morwet D425) | 5.0000 |
| Wetting agent (Supragil WP) | 3.0000 |
| Dye(s) | 0.0500 |
| Fillers (s) (Wessalon-S and Kaolex) | 70.1698 |
| Total | 100.00% (w/w) |

Process for the preparation of the above said synergistic insecticidal composition comprises mixing thoroughly, for ½ hour, Acetamiprid, PBO, Bitrex, Morwet D425, Supragil WP, Wessalon-S, Kaolex, Fenvalerate and Rhodamine-B in a pre-blender equipped with an agitator to get a homogenous mixture of all the ingredients. Thereafter, the homogenous mixture obtained is micronised to get a particle size of 2-10 microns which is post-blended to yield the synergistic insecticidal composition.

EXAMPLE-7

Process for the preparation of a synergistic insecticidal composition containing Imidacloprid 4.5%+Cypermethrin 15.0% [19.5% DF]:

Composition

| Ingredient | Quantity (% w/w) |
|---|---|
| Imidacloprid Techical (purity 95%) | 4.7400 |
| Cypermethrin Technical (purity 92%) | 16.3000 |
| Stabilizer (PBO) | 0.2000 |
| Emetic agent (Bitrex) | 0.0003 |

-continued

| Ingredient | Quantity (% w/w) |
|---|---|
| Disintegrating agent (Zeolite) | 5.0000 |
| Antifoaming agent (Antimousse 426-R) | 0.0500 |
| Wetting cum dispersing agent (Lisapol-D) | 13.0000 |
| Sticking agent (PVP K 30) | 1.0000 |
| Dye(s) (Rhodamine B) | 0.0500 |
| Fillers (s) (Insilco and Kaolex) | 59.6597 |
| Total | 100.00% (w/w) |

The process for the preparation of the above synergistic insecticidal composition comprises mixing thoroughly, for ½ hour, Imidacloprid, PBO, antimousse 426-R, Lisapol D, Insilco, Kaolex, Cypermethrin, Bitrex, Zeolite, and Rhodamine B, PVP-K-30 in a pre-blender equipped with an agitator to get a homogenous mixture of all the ingredients. Thereafter, the homogenous mixture obtained is micronised to get a particle size of 2-10 microns which is post-blended and thereafter granulated, conditioned, sized and sieved to yield the synergistic insecticidal composition.

EXAMPLE-8

Process for the preparation of a synergistic insecticidal composition containing Acetamaprid 2.0%+Cypermethrin 10.0% [12.0% DF]:

Composition

| Ingredient | Quantity (% w/w) |
|---|---|
| Acetamaprid Techical (purity 95%) | 2.1100 |
| Cypermethrin Technical (purity 92%) | 1.8700 |
| Stabilizer (PBO) | 0.2000 |
| Emetic agent (Bitrex) | 0.0003 |
| Disintegrating agent (Zeolite) | 5.0000 |
| Antifoaming agent (Antimousse 426-R) | 0.0500 |
| Wetting cum dispersing agent (Lisapol-D) | 13.0000 |
| Sticking agent (PVP K 30) | 1.0000 |
| Dye(s) (Rhodamine B) | 0.0500 |
| Fillers (s) (Insilco and Kaolex) | 67.7197 |
| Total | 100.00% (w/w) |

The process for the preparation of the above synergistic insecticidal composition comprises mixing thoroughly, for ½ hour, Acetamaprid, PBO, antimousse 426-R, Lisapol D, Insilco, Kaolex, Cypermethrin, Bitrex, Zeolite, and Rhodamine B, PVP-K-30 in a pre-blender equipped with an agitator to get a homogenous mixture of all the ingredients. Thereafter, the homogenous mixture obtained is micronised to get a particle size of 2-10 microns which is post-blended and thereafter granulated, conditioned, sized and sieved to yield the synergistic insecticidal composition.

EXAMPLE-9

Process for the preparation of a synergistic insecticidal composition containing Imidacloprid 4.0%+Permethrin 20.0% [24.0% DF]:

Composition

| Ingredient | Quantity (% w/w) |
|---|---|
| Imidacloprid Techical (purity 95%) | 4.2100 |
| Permethrin Technical (purity 92%) | 21.7400 |

-continued

| Ingredient | Quantity (% w/w) |
|---|---|
| Stabilizer (PBO) | 0.2000 |
| Emetic agent (Bitrex) | 0.0003 |
| Disintegrating agent (Zeolite) | 5.0000 |
| Antifoaming agent (Antimousse 426-R) | 0.0500 |
| Wetting cum dispersing agent (Lisapol-D) | 13.0000 |
| Sticking agent (PVP K 30) | 1.0000 |
| Dye(s) (Rhodamine B) | 0.0500 |
| Fillers (s) (Insilco and Kaolex) | 54.7497 |
| Total | 100.00% (w/w) |

The process for the preparation of the above synergistic insecticidal composition comprises mixing thoroughly, for ½ hour, Imidacloprid, PBO, antimousse 426-R, Lisapol D, Insilco, Kaolex, Permethrin, Bitrex, Zeolite, and Rhodamine B, PVP-K-30 in a pre-blender equipped with an agitator to get a homogenous mixture of all the ingredients. Thereafter, the homogenous mixture obtained is micronised to get a particle size of 2-10 microns which is post-blended and thereafter granulated, conditioned, sized and sieved to yield the synergistic insecticidal composition.

EXAMPLE-10

Process for the preparation of a synergistic insecticidal composition containing Imidacloprid 4.5%+Cypermethrin 15.0% [19.5% EC]:

Composition

| Ingredient | Quantity (% w/w) |
|---|---|
| Imidacloprid Techical (purity 95%) | 4.7400 |
| Cypermetrin Technical (purity 92%) | 16.3000 |
| Stabilizer (PBO) | 0.1000 |
| Emetic agent (Amrex) | 0.0002 |
| Emulsifier (Rhodocal 65 BR &Igepol) | 10.0000 |
| Dye(s) (RGB) | 0.1000 |
| Cosolvent (DMSO) | 10.0000 |
| Diluent(aromatic hydrocarbon Solvesso-200) | 58.7598 |
| Total | 100.00% (w/w) |

The process of preparing the above synergistic insecticidal composition comprises stirring thoroughly, for 1 hour, Imidacloprid, Cypermethrin, PBO, Amrex, RGB, DMSO, Solvesso-200 in the above said proportions in a vessel equipped with an agitator to get a homogenous solution of all the ingredients. Thereafter, the homogenous solution (Blank) obtained is analyzed for the requirement of different ratios emulsifier to get good emulsification. After ratio setting, the emulsifier is added in the vessel, in calculated quantities, equipped with an agitator and homogenised for 1 hr to yield the synergistic insecticidal composition.

EXAMPLE-11

Process for the preparation of a synergistic insecticidal composition containing Imidacloprid 2.0%+Fenvalerate 15.0% [17.0% EC]:

Composition

| Ingredient | Quantity (% w/w) |
|---|---|
| Imidacloprid Techical (purity 95%) | 2.1100 |
| Fenvalerate Technical (purity 92%) | 16.3000 |
| Stabilizer (PBO) | 0.1000 |
| Emetic agent (Amrex) | 0.0002 |
| Emulsifier (Rhodocal 65 BR &Igepol) | 10.0000 |
| Dye(s) (RGB) | 0.1000 |
| Cosolvent (DMSO) | 05.0000 |
| Diluent(aromatic hydrocarbon Solvesso-200) | 66.3898 |
| Total | 100.00% (w/w) |

The process of preparing the above synergistic insecticidal composition comprises stirring thoroughly, for 1 hour, Imidacloprid, Fenvalerate, PBO, Amrex, Ocean Blue, DMSO, Solvesso-200 in the above said proportions in a vessel equipped with an agitator to get a homogenous solution of all the ingredients. Thereafter, the homogenous solution (Blank) obtained is given for emulsifier ratio setting to get good emulsification. After ratio setting, mix the calculated quantity of emulsifier to the vessel equipped with an agitator. Mix for 1 hr to yield the synergistic insecticidal composition.

EXAMPLE-12

Process for the preparation of a synergistic insecticidal composition containing Imidacloprid 2.5%+Permethrin 10.0% [12.5% EC]:

Composition

| Ingredient | Quantity (% w/w) |
|---|---|
| Imidacloprid Techical (purity 95%) | 2.6300 |
| Permethrin Technical (purity 92%) | 10.8700 |
| Stabilizer (PBO) | 0.1000 |
| Emetic agent (Amrex) | 0.0002 |
| Emulsifier (Rhodocal 65 BR &Igepol) | 10.0000 |
| Dye(s) (RGB) | 0.1000 |
| Cosolvent (DMSO) | 5.0000 |
| Diluent(aromatic hydrocarbon Solvesso-200) | 71.2998 |
| Total | 100.00% (w/w) |

The process of preparing the above synergistic insecticidal composition comprises stirring thoroughly, for 1 hour, Imidacloprid, Permethrin, PBO, Amrex, Ocean Blue, DMSO, Solvesso-200 in the above said proportions in a vessel equipped with an agitator to get a homogenous solution of all the ingredients. Thereafter, the homogenous solution (Blank) obtained is given for emulsifier ratio setting to get good emulsification. After ratio setting, mix the calculated quantity of emulsifier to the vessel equipped with an agitator. Mix for 1 hr to yield the synergistic insecticidal composition.

EXAMPLE-13

Evaluation of the synergistic insecticidal effect of the Chloronicotynyle compound (Imidacloprid, Acetamiprid) plus a second insecticide Pyrethroids compound (Cypermethrin, Fenvalerate, Permethrin) can be established by using any synergistic insecticidal composition prepared by the process described in the above examples. For these evaluations one or more of the synergistic insecticidal compositions prepared in the examples are used here.

In this evaluation, Brown plant hoppers and Green plant hoppers are obtained from laboratory colonies. Paddy leaves are immersed in 1:1 v/v, acetone/water solutions of the test compound, or solution of a combination of the test compounds for a period of about 4 seconds. Following immersion, leaves are allowed to air-dry for 2-3 hours. Plastic bioassay trays containing multiple open-faced wells (4.0×4.0×2.5 cm) are used. Cut portions of a treated leaf, a moistened cotton dental wick and a single third-instar larva are placed into each well. These wells are covered with an adhesive vented clear plastic sheet which is held under constant fluorescent light at about 30° C. for a predetermined period of time. Larval mortality/morbidity is evaluated at 5 days after treatment. All treatments are replicated 3-4 fold in a randomized complete block design with 15-30 larvae per treatment. Using conventional log-probit analysis, the $LC_{50}$ of each treatment is determined.

Using the above process, a Chloronicotynyle compound may be evaluated alone and in combination with a second insecticidal compound, including Imidacloprid and Acetamiprid, at dose rates of 0, 15, 18, 21, 24, 27 and 30 ppm and in combination with Cypermethrin, Fenvalerate, Permethrin 0, 70, 80, 85, 90, 100 ppm in various combination of these strengths. Treatments which are used are shown in following Table 1.

TABLE 1

| Second active compound | Dose Rate (ppm) | Imidacloprid Dose Rate (ppm) | | | | | |
|---|---|---|---|---|---|---|---|
| Cypermethrin/Permethrin | 0 | 0 | 15 | 18 | 21 | 24 | 27 | 30 |
| | 70 | 0 | 15 | 18 | 21 | 24 | 27 | 30 |
| | 80 | 0 | 15 | 18 | 21 | 24 | 27 | 30 |
| | 85 | 0 | 15 | 18 | 21 | 24 | 27 | 30 |
| | 90 | 0 | 15 | 18 | 21 | 24 | 27 | 30 |
| | 100 | 0 | 15 | 18 | 21 | 24 | 27 | 30 |

1 ppm (parts per million) = 0.0001%

The results of the above experiment show that out of a large number of the combinations tried, some of them show synergistic insecticidal control.

The following example confirms the synergistic effect of the strength selected from Example-13.

EXAMPLE-14

Synergism can be calculated by using the Colby's method i.e. the expected (or predicted) response of the combination is calculated by taking the product of the observed response for each individual component of the combination when applied alone divided by 100 and subtracting this value from the sum of observed response for each component when applied alone. Synergism of the combination is then determined by comparing the observed response of the combination to the expected (or predicted) response as calculated from the observed response of each individual component alone. If the observed response of the combination is greater than the expected (or predicted) response, then the combination is said to be synergistic and falls within the definition of synergistic effect. (Colby, S. R., Weeds, 1967(15), p. 20-22)

TABLE 2

Synergistic insecticidal effect of a combination of Imidacloprid + Cypermethrin

| S. No. | Imidacloprid (ppm) | Cypermethrin (ppm) | Observed Mortality % | Expected Mortality % | Difference |
|---|---|---|---|---|---|
| 1 | 24 | 0 | 55.00 | — | — |
| 2 | 27 | 0 | 69.25 | — | — |
| 3 | 30 | 0 | 72.10 | — | — |
| 4 | 0 | 80 | 52.5 | — | — |
| 5 | 0 | 85 | 60 | — | — |
| 6 | 0 | 90 | 70 | — | — |
| 7 | 24 | 80 | 70.00 | 78.63 | −8.63 |
| 8 | 24 | 85 | 92.75 | 82.00 | 10.75 |
| 9 | 24 | 90 | 93.00 | 86.50 | 6.50 |
| 10 | 27 | 80 | 88.8 | 85.40 | 2.60 |
| 11 | 27 | 85 | 91.00 | 87.70 | 3.30 |
| 12 | 27 | 90 | 97.05 | 90.78 | 6.27 |
| 13 | 30 | 80 | 90.00 | 86.75 | 3.25 |
| 14 | 30 | 85 | 95.00 | 88.84 | 6.16 |
| 15 | 30 | 90 | 99.5 | 91.63 | 7.87 |

As can be seen from the data shown in Table 2, combinations of Imidacloprid plus a Pyrethroids compound (Cypermethrin) demonstrate synergistic insect control.

TABLE 3

Synergistic insecticidal effect of a combination of Acetamiprid + Cypermethrin

| S. No. | Acetamiprid (ppm) | Cypermethrin (ppm) | Observed Mortality % | Expected Mortality % | Difference |
|---|---|---|---|---|---|
| 1 | 24 | 0 | 47.30 | — | — |
| 2 | 27 | 0 | 69.25 | — | — |
| 3 | 30 | 0 | 72.1 | — | — |
| 4 | 0 | 80 | 60.0 | — | — |
| 5 | 0 | 85 | 65 | — | — |
| 6 | 0 | 90 | 72.0 | — | — |
| 7 | 24 | 80 | 83.03 | 78.92 | 4.11 |
| 8 | 24 | 85 | 88.91 | 81.56 | 7.41 |
| 9 | 24 | 90 | 91.04 | 85.24 | 5.80 |
| 10 | 27 | 80 | 89.00 | 87.70 | 1.30 |
| 11 | 27 | 85 | 92.03 | 89.24 | 2.79 |
| 12 | 27 | 90 | 94.00 | 91.39 | 2.61 |
| 13 | 30 | 80 | 93.00 | 88.84 | 4.16 |
| 14 | 30 | 85 | 95.00 | 90.24 | 4.76 |
| 15 | 30 | 90 | 98.00 | 92.19 | 5.81 |

As can be seen from the data shown in Table 3, combinations of Acetamprid plus a Pyrethroids compound (Cypermethrin) demonstrate synergistic insect control.

EXAMPLE 15

The following is an evaluation of the synergistic insecticidal effect of a combination of a Chloronicotynyle compound (Imidacloprid) plus a Pyrethroids compound (Cypermethrin) against pests of Paddy. In this example most of the synergistic insecticidal compositions prepared by the process described in this invention are used to evaluate their activities.

In this evaluation, per cent mortality of hoppers is worked out based on the number of hoppers counted before and after sprays and based on dead heart counts before and after sprays. The data is averaged and analyzed for the test of significance.

Details of the Experiment
a. Design: Randomised block design
b. Replication: Three
c. Product: Imidacloprid+Cypermethrin (4.5+15) %
d. Treatment: Seven (as shown in details in the Table -4)

TABLE 4

(Details of the treatments done)

| S. No. | Active Ingredient (g a.i./ha) dose | Formulation quantity (g/ha) |
|---|---|---|
| 1 | Imidacloprid + Cypermethrin 39 | 200 |
| 2 | Imidacloprid + Cypermethrin 58.5 | 300 |
| 3 | Imidacloprid + Cypermethrin 78 | 400 |
| 4 | Imidacloprid + Cypermethrin 97.5 | 500 |
| 5 | Imidacloprid 17.8% SL 20 | 112 |
| 6 | Cypermethrin 25% EC 60 | 240 |
| 7 | Water spray only | |

Imidacloprid+Cypermethrin(4.5+15) % at 800 and 1600 g/ha laid out separately by the side of bio-efficacy trial plot to avoid drift of chemical.
e. Plot size: 5×4 m=20 sq.m.
f. Variety: Jyothi
g. Spacing: 20×10 cm
h. Fertilizer: 100:50:50 NPK Kg/ha
i. Sprayer used: Knapsack sprayer
j. Spray volume: 1.5 liter per 20 sq. m. plot
k. Time of application: When the hoppers and dead heart symptom are noticed.
l. Method: Required quantity of spray fluid is prepared before spray application and for phytotoxicity studies concentration of Imidacloprid+Cypermethrin (405+15) % at 800 and 1600 g/ha is laid out separately by the side of the bio-efficacy trial plot to avoid drift of the chemical.
m. Observations recorded:
  i. Pre and post treatment data of green leaf hopper in three leaves from the base, middle and top position of the plants, brown plant hoppers on the stem portions.
  ii. Phytotoxicity of higher concentrations.
  iii. Grain yield.
n. Method of Observation: Phytotoxicity in terms of yellowing or blightening of leaves is recorded in the higher concentrations of 800 and 1600 g/ha. When the crop-attained maturity the ear heads are harvested, dried, threshed and grain yield per 20 sq. m. plot is recorded and it is then computed to quintals per hectare. The data is analyzed statistically to discriminate the treatment superiority for control leaf eating pests and variation in the yield.
o. Results: The results of the field trial carried out to evaluate the bioefficacy of and standardization of doses of Imidacloprid+Cypermethrin (4.5+15) % at doses 200, 300, 400, 500 g/ha as compared Imidacloprid 17.8% SL 20 g/ha, Cypermethrin 25% Ec 240 g/ha and untreated check are presented in the following tables.

TABLE 5

Mortality (%) Brown plant hoppers on days after Imidacloprid + Cypermethrin (4.5 + 15)% spray application at various application/treatment dose

| Sr. No. | Treatment (g/ha) | Pre-count (numbers) | Mortality % 10 DAT after I spray | Pre-count (Numbers) | % 10 DAT after II spray | Mean % Mortality due to two sprays |
|---|---|---|---|---|---|---|
| 1 | Imidacloprid + Cypermethrin (200) | 16.77 | 70.16 | 11.00 | 68.00 | 69.05 |

TABLE 5-continued

Mortality (%) Brown plant hoppers on days after Imidacloprid + Cypermethrin (4.5 + 15)% spray application at various application/treatment dose

| Sr. No. | Treatment (g/ha) | Pre-count (numbers) | Mortality % 10 DAT after I spray | Pre-count (Numbers) | % 10 DAT after II spray | Mean % Mortality due to two sprays |
|---|---|---|---|---|---|---|
| 2 | Imidacloprid + Cypermethrin (300) | 11.68 | 71.15 | 10.20 | 70.10 | 70.62 |
| 3 | Imidacloprid + Cypermethrin (400) | 15.18 | 72.16 | 10.70 | 72.20 | 72.15 |
| 4 | Imidacloprid + Cypermethrin (500) | 13.10 | 72.20 | 9.60 | 72.50 | 72.55 |
| 5 | Imidacloprid 17.8% SL (112) | 18.07 | 70.16 | 11.00 | 68.50 | 69.33 |
| 6 | Cypermethrin 25% EC (240) | 16.66 | 70.50 | 10.10 | 69.00 | 69.75 |
| 7 | Water Spray | 18.20 | −30.69 | 19.10 | −32.10 | −31.40 |

TABLE 6

Mortality (%) of green plant hoppers on days after spray application of Imidacloprid + Cypermethrin (4.5 + 15)%

| Sr. No. | Treatment (g/ha) | Pre-count Numbers) | Mortality % 10 DAT after I spray | Pre-count (Numbers) | Mortality % 10 DAT after II spray | Mean % Mortality due to two sprays |
|---|---|---|---|---|---|---|
| 1 | Imidacloprid + Cypermethrin (200) | 8.6 | 65 | 6.33 | 64.00 | 64.50 |
| 2 | Imidacloprid + Cypermethrin (300) | 8.40 | 66.13 | 6.88 | 62.16 | 64.24 |
| 3 | Imidacloprid + Cypermethrin (400) | 9.46 | 70.10 | 9.00 | 64.15 | 67.12 |
| 4 | Imidacloprid + Cypermethrin (500) | 8.60 | 78.10 | 8.60 | 70.35 | 74.22 |
| 5 | Imidacloprid 17.8% SL (112) | 7.60 | 70.10 | 6.65 | 69.66 | 69.88 |
| 6 | Cypermethrin 25% EC (240) | 8.64 | 69.66 | 8.30 | 68.70 | 69.18 |
| 7 | Water Spray | 7.16 | −8.50 | 8.15 | −16.15 | −12.33 |

Conclusion

From Table-5 and 6, the results of the field trial carried out to evaluate the bioefficacy of and standardization of doses of the synergistic insecticidal composition at doses of 200, 300, 400 and 500 g/ha as compared with Imidacloprid 17.8% SL, Cypermethrin 25% EC-240 ml/ha and untreated check are presented. Mortality of Brown plant hoppers increased with increase in the concentrations of synergistic insecticidal composition from 200 to 500 g/ha and which was on par with the other chemicals tested, see Table 5. Against green leaf hoppers, see Table 6, maximum mortality was recorded in composition @500 g and 400 g/ha. It was on par with standard checks. However, the synergistic insecticidal composition @ 300 g was least effective with little variation after the second spray.

TABLE 7

Reduction (%) of dead hearts due to stem borer after Imidacloprid + Cypermethrin (4.5 + 15)% pesticide application in different strength

| Sr. No. | Treatment (g/ha) | Pre-count (Numbers) | Reduction of dead hearts % after I spray | Reduction of dead hearts % after II spray | Mean % reduction of dead hearts after two spray |
|---|---|---|---|---|---|
| 1 | Imidacloprid + Cypermethrin (200) | 6.23 | 56.00 | 58.00 | 57.00 |
| 2 | Imidacloprid + Cypermethrin (300) | 9.81 | 58.12 | 69.00 | 63.56 |
| 3 | Imidacloprid + Cypermethrin (400) | 8.98 | 62.35 | 72.00 | 67.18 |
| 4 | Imidacloprid + Cypermethrin (500) | 11.11 | 66.12 | 76.00 | 71.06 |
| 5 | Imidacloprid 17.8% SL (112) | 8.18 | 67.12 | 79.00 | 73.06 |
| 6 | Cypermethrin 25% EC (240) | 7.60 | 68.15 | 68.00 | 68.08 |
| 7 | Water Spray | 9.20 | −1.80 | −7.80 | −4.80 |

Conclusion

From Table-7 against stem borers, the synergistic insecticidal composition containing Imidacloprid+Cypermethrin at all concentrations proved next best to standard checks after first spray and next best to imidacloprid after the second spray, see Table 7.

TABLE 8

Grain yield after spray application of Imidacloprid + Cypermethrin (4.5 + 15)% in different strength

| Sr. No. | Treatment (g/ha) | Grain yield (qtl/ha) |
|---|---|---|
| 1 | Imidacloprid + Cypermethrin (200) | 128.35 |
| 2 | Imidacloprid + Cypermethrin (300) | 129.60 |
| 3 | Imidacloprid + Cypermethrin (400) | 144.20 |
| 4 | Imidacloprid + Cypermethrin (500) | 145.95 |

TABLE 8-continued

Grain yield after spray application of Imidacloprid + Cypermethrin (4.5 + 15)% in different strength

| Sr. No. | Treatment (g/ha) | Grain yield (qtl/ha) |
|---|---|---|
| 5 | Imidacloprid 17.8% SL (112) | 92.00 |
| 6 | Cypermethrin 25% EC (240) | 123.26 |
| 7 | Water Spray | 77.50 |

Conclusion

Grain yield levels, as shown in Table-8 @ 400 and 500 g followed by 300 and 200 g were on par with Cypermethrin and superior over Imidacloprid, see Table 8.

TABLE 9

Phytotoxicity due to application of Imidacloprid + Cypermethrin (4.5 + 15)% pesticides in different strengths

| Sr. No. | Treatment (Dose g/ha) | Dose g a.i./ha | *Cumulative Phytotoxicity (%) on 14th day |
|---|---|---|---|
| 1 | Imidacloprid + Cypermethrin (200) | 39 | NP |
| 2 | Imidacloprid + Cypermethrin (300) | 58.5 | NP |
| 3 | Imidacloprid + Cypermethrin (400) | 78 | NP |
| 4 | Imidacloprid + Cypermethrin (500) | 97.5 | NP |
| 5 | Imidacloprid + Cypermethrin (800) | 156 | 2.00% |
| 6 | Imidacloprid + Cypermethrin (1600) | 312 | 3.00% |
| 7 | Imidacloprid 17.8 SL (112) | 60 | NP |
| 8 | Cypermethrin 25% EC (240) | 60 | NP |
| 9 | Water spray | — | NP |

NP = No phytoxocity
*= Observation for phytoxicity was taken for 14 days after spray on necrosis, hyponasty, leaf tip injury, leaf surface injury, wilting, vein clearing etc.

Results

The synergistic insecticidal composition containing Imidacloprid and Cypermethrin is effective against brown plant hopper which was increased with increased concentrations from 200 to 500 g/ha. Synergistic insecticidal composition at 500 g proved superior against green leaf hoppers. Synergistic insecticidal composition @ 500 g/ha proved next best treatment to standard checks against stem borers.

The superiority of the synergistic insecticidal composition including Imidacloprid and Cypermethrin reflected in highest grain yields at 400 & 500 g/ha.

The synergistic insecticidal composition prepared by the process of this invention can be applied as per prescribed recommendation on the label by mixing the pesticide and water at the right dosage and spray. It can be sprayed by using high volume sprayer viz. Knapsack sprayer, using 500-1000 liters of water per hactare.

Although the present invention has been disclosed in terms of a preferred embodiment, it will be understood that numerous additional modifications and variations could be made thereto without departing from the scope of the invention as defined by the following claims:

We claim:

1. A synergistic insecticidal composition comprising
   a) a synergistically effective amount of Imidacloprid in an amount of about 4.5 wt.% of the composition,
   b) a synergistically effective amount of Cypermethrin in an amount of a about 15 wt.% of the composition, and the balance of the composition being
   c) conventional agriculturally acceptable carriers and excipients the total weight of a,b, and c constituting 100% of the composition, and
   wherein Imidacloprid and Cypermethrin are the only insecticidally active ingredients in said composition.

2. The synergistic insecticidal composition of claim 1, wherein the synergistic insecticidal composition is in the form of an aqueous formulation or dry based formulations.

3. The synergistic insecticidal composition of claim 1, whereby said composition kills green leaf hoppers and brown plant hoppers.

4. The synergistic insecticidal composition of claim 1, whereby said composition protects paddy plants from insects.

5. The synergistic insecticidal composition of claim 1, whereby said composition is applied to a plant at a concentration of from 200 to 500 g/ha.

6. The synergistic composition of claim 5, whereby said composition is applied to a plant at a concentration of from 400 to 500 g/ha.

7. The synergistic insecticidal composition of claim 1 wherein the agriculturally acceptable carrier or excipient is selected from the group consisting of silicas, silica gels, silicates, talc, kaolin, montmorillonite, attapulgite, pumice, sepiolite, bentonite, limestone, lime, chalk, clay, dolomite, diatomaceous earth, calcite, calcium sulfate, magnesium sulfate, magnesium sulfate, magnesium oxide, sand, ammonium sulfate, ammonium phosphat, ammonium nitrate, crushed products of vegetable origin, cereal meal, tree bark meal, wood meal, nutshell meal, and cellulose powders.

8. The synergistic insecticidal composition of 1, wherein said agriculturally acceptable carrier or excipient is a liquid carrier selected from the group consisting of aromatics, xylene, toluene, alkylnaphthalenes, chlorinated aromatics, chlorinated aliphatic hydrocarbons, chlorobenzenes, chloroethylenes, methylene chloride, aliphatic hydrocarbons, cyclohexane, paraffins, mineral oil fractions, alcohols, butanol, glycol, ethers and esters, ketones, acetone, methyl ethyl ketone, methyl isobutyl ketone, cyclohexanone, strongly polar solvents, dimethylformamide, dimethyl sulphoxide, water, and aromatic hydrocarbon solvents.

9. The synergistic insecticidal composition of claim 1, further comprising a gaseous carrier, said gaseous carrier is a liquified gaseous extenders or a carrier that is gaseous at ambient temperature and under atmospheric pressure.

10. The synergistic insecticidal composition of claim 9, wherein said gaseous carrier is selected from the group consisting of an aerosol propellant, a halogenated hydrocarbons, butane, propane, nitrogen and carbon dioxide, water, alcohols, ketones, petroleum fractions, aromatic or paraffinic hydrocarbons, chlorinated hydrocarbons, and liquefied gases.

11. The synergistic insecticidal composition of claim 1 further comprising a surfactant.

12. The synergistic insecticidal composition of claim 11, wherein said surfactant is selected from the group consisting of a non-ionic surfactant, a cationic surfactant and an anionic surfactant.

13. The synergistic insecticidal composition of claim 12, wherein said anionic surfactants is selected from the group consisting of a water-soluble soap, a water-soluble synthetic surface-active compound, an alkali metal soap, an alkaline earth metal soap, a substituted or unsubstituted ammonium salts of a higher fatty acid, the sodium or potassium salt of oleic or stearic acid, a natural fatty acid mixtures.

14. The synergistic insecticidal composition of claim 11, wherein the surfactant is a salt of polyacrylic acids, a salt of lignosulphonic acids, a salt of phenylsulphonic, a naphthalene sulphonic acid, polycondensates of ethylene oxide with fatty alcohols or with fatty acids or with fatty amines, substituted phenols, alkylphenols, arylphenols, sulphosuccinic ester salts, taurine derivatives, alkyltaurates, a phosphoric ester of polyethoxylated phenols or alcohols.

15. The synergistic insecticidal composition of claim 1, further comprising a stabilizer.

16. The synergistic insecticidal composition of claim 15 wherein the stabilizer is selected from a group consisting of Piperonyl butoxide, ethoxylate of vegetable oil, salts of higher fatty acids, a blend of the derivatives of epoxylated vegetable oil, Ethoxylated polyoxyethylene amine, pyroolidine, and lactone.

17. The synergistic insecticidal composition of claim 1, further comprising a wetting cum dispersing agent.

18. The synergistic insecticidal composition of claim 17 wherein the wetting cum dispersing agent is selected from a group consisting of Alkyl Phenol Ethoxylate, salts of alkyl naphthyl sulphonate, salts of alkyl aryl sulphonate, and derivative of sulfonated fatty alcohol.

19. The synergistic insecticidal composition of claim 1 further comprising a wetting agent.

20. The synergistic insecticidal composition of claim 19 wherein the wetting agent is calcium or sodium salt(s) of alkyl aryl sulphonate.

21. The synergistic insecticidal composition of claim 1 further comprising a dispersing agent.

22. The synergistic insecticidal composition of claim 21, wherein the dispersing agent used is formaldehyde condensate of alkyl phenols.

23. The synergistic insecticidal composition of claim 1 further comprising an emetic agent.

24. The synergistic insecticidal composition of claim 23, wherein the emetic agent is a lignocaine derivative or a formulation of lignocaine derivative.

25. The synergistic insecticidal composition of claim 1, further comprising a dye or colorant.

26. The synergistic insecticidal composition of claim 25, wherein said dye or colorants is a water soluble or water insoluble dye or inorganic pigment.

27. The synergistic insecticidal composition of claim 25, wherein said dye or colorant is selected from the group consisting of iron oxide, titanium oxide, Prussian Blue, Rhodamine -B, alizarin dyestuffs, azo dyestuffs, metal phthalocyanine dyestuffs, salts of iron, salts of manganese, salts of boron, salts of copper, salts of cobalt, salts of molybdenum, and salts of zinc.

28. The synergistic insecticidal composition of claim 1, further comprising an antifoaming agent.

29. The synergistic insecticidal composition of claim 28, wherein said antifoaming agent is silicone oil derivative.

30. The synergistic insecticidal composition of claim 1, further comprising a disintegrating agent.

31. The synergistic insecticidal composition of claim 30, wherein the disintegrating agent is selected from a group consisting of bentonite clay, Zeolite clay, Attapulgite clay, and sodium sulphate salts, and Aluminium sulphate salts.

32. The synergistic insecticidal composition of claim 1, further comprising a filler.

33. The synergistic insecticidal composition of claim 32, wherein the filler is selected from a group consisting of silica, kaoline, and clay.

34. The synergistic insecticidal composition of claim 1, wherein said carrier and said excipient are present in a carrier/excipient ratio ranging from 1:1 to 1:10000.

35. The synergistic insecticidal composition of claim 1, further comprising an anticaking agent.

36. The synergistic insecticidal composition of claim 35, wherein the anticaking agent is selected from a group consisting of fumed silica, anhydrous Magnesium sulphate, and a blend of sucrose and starch derivatives.

37. The synergistic insecticidal composition of claim 1, further comprising a binding agent.

38. The synergistic insecticidal composition of claim 37, wherein the binding agent is a pyrralidone derivative.

39. The synergistic insecticidal composition of claim 1, wherein the synergistic insecticidal composition has an average particle size of 2-1500 microns.

40. The synergistic insecticidal composition of claim 39, wherein synergistic insecticidal composition has particle size of 501500 microns.

41. The synergistic insecticidal composition of claim 1, wherein the Cypermethrin is a Technical grade Cypermethrin having a purity of 92% minimum.

42. The synergistic insecticidal composition of claim 1, wherein the Imidacloprid is a Technical grade Imidacloprid having a purity of 95% minimum.

* * * * *